US012774208B2

(12) United States Patent
Je et al.

(10) Patent No.: US 12,774,208 B2
(45) Date of Patent: Oct. 27, 2026

(54) METHOD FOR MANUFACTURING CORE-SHELL NANOWIRE AND NANOWIRE MANUFACTURED THEREBY

(71) Applicant: POSTECH RESEARCH AND BUSINESS DEVELOPMENT FOUNDATION, Pohang-si (KR)

(72) Inventors: Jung Ho Je, Pohang-si (KR); Seung Soo Oh, Pohang-si (KR); Moon Jung Yong, Incheon (KR); Un Yang, Pohang-si (KR)

(73) Assignee: POSTECH RESEARCH AND BUSINESS DEVELOPMENT FOUNDATION, Pohang-si (KR)

(*) Notice: Subject to any disclaimer, the term of this patent is extended or adjusted under 35 U.S.C. 154(b) by 1020 days.

(21) Appl. No.: 17/792,344

(22) PCT Filed: Jan. 30, 2020

(86) PCT No.: PCT/KR2020/001385
§ 371 (c)(1),
(2) Date: Jul. 12, 2022

(87) PCT Pub. No.: WO2021/153817
PCT Pub. Date: Aug. 5, 2021

(65) Prior Publication Data
US 2023/0050510 A1 Feb. 16, 2023

(30) Foreign Application Priority Data
Jan. 29, 2020 (KR) ........................ 10-2020-0010496

(51) Int. Cl.
*B81C 1/00* (2006.01)
*A61K 9/00* (2006.01)

(52) U.S. Cl.
CPC ........ *B81C 1/00206* (2013.01); *A61K 9/0092* (2013.01)

(58) Field of Classification Search
CPC .............................. B81C 1/00206; H01B 5/00
See application file for complete search history.

(56) References Cited

U.S. PATENT DOCUMENTS

2012/0298401 A1* 11/2012 Je .............................. H01B 5/00 174/126.1

FOREIGN PATENT DOCUMENTS

KR 20160000281 1/2016
KR 20180108226 10/2018
(Continued)

OTHER PUBLICATIONS

An, et al., Nanomeniscus-induced delivery of liquid solutions for diverse nanofiber fabrication, Nano Convergence, 2015, vol. 2, No. 13, pp. 1-7.
(Continued)

*Primary Examiner* — Robert S Walters, Jr.
*Assistant Examiner* — Andrew J Bowman
(74) *Attorney, Agent, or Firm* — CANTOR COLBURN LLP

(57) ABSTRACT

Provided is a method of fabricating a core-shell structured nanowire on a tip of an optical fiber, on a substrate, or any position on other target objects, and a nanowire fabricated by the method. The nanowire fabricated by the method of the present invention may be used for a drug delivery system, a sensor, an optical waveguide, and the like.

13 Claims, 6 Drawing Sheets

(56) References Cited

FOREIGN PATENT DOCUMENTS

| | | | | | |
|---|---|---|---|---|---|
| KR | 20190071964 | | | 6/2019 | |
| KR | 20190071964 | A | * | 6/2019 | ............... G02B 6/02 |

OTHER PUBLICATIONS

International Search Report—PCT/KR2020/001385 dated Oct. 21, 2020.

Won, et al., Polymer composite microtube array produced by meniscus-guided approach, AIP Advances, Sep. 2013, vol. 3, Article No. 092127.

* cited by examiner (a) (b)

(c)

(a) (b)

METHOD FOR MANUFACTURING CORE-SHELL NANOWIRE AND NANOWIRE MANUFACTURED THEREBY

TECHNICAL FIELD

The present invention relates to a method of fabricating a core-shell structured nanowire on a tip of an optical fiber, on a substrate, or at any position on other target objects. Moreover, the present invention relates to a drug delivery system, a sensor, etc., which include the nanowire fabricated by the method.

BACKGROUND ART

The term "core-shell nanowire" refers to a nanowire having a structure in which a core of the nanowire is covered by a shell of another material. The core and shell of different materials have different properties (hydrophilicity/hydrophobicity, biodegradability, electrical conductivity, etc.). Therefore, many studies on these properties of core-shell nanowires have been conducted in various fields, including drug delivery, sensors, and batteries.

For example, core-shell nanowires can be used as a medium for drug delivery, and technologies have been developed that incorporate a drug to be delivered in the core and control the release of the drug, incorporated in the core, through the shell (Hongliang Jian et al., Journal of Controlled Release, 2014, 193, pp 296-303). Further, sensor fabrication technology using a shell capable of reacting with a target material has also been studied (Daewoo Han et al., ACS applied materials & interfaces, 2017, 9(13), pp 11858-11865). In addition, studies have been conducted to increase the efficiency of a solar cell by increasing the surface area thereof through a core-shell nanowire array (Zhen Liu et al., Chemical Communications, 2012, 48(22), pp 2815-2817).

A conventional method for fabricating a core-shell nanowire is based on a coaxial electrospinning method. FIG. 1(*a*) is a view showing a coaxial electrospinning method of fabricating a core-shell nanowire by allowing an inner fluid to be discharged by a potential difference between a coaxial needle and a collector. FIG. 1(*b*) shows core-shell nanowires randomly arranged on a substrate by coaxial electrospinning. The coaxial electrospinning method can produce a large amount of core-shell nanowires at the same time, but has problems in that materials usable in the method are limited to the polymer having charges, and in that it is difficult to adjust the length and arrangement of the nanowires. Therefore, there is a limit to fabricating a device having a specific microstructure or to developing a technology for transferring or sensing a material in a local section of a few micrometers.

Another conventional method for fabricating a core-shell nanowire is based on deposition. FIG. 1(*c*) is a view showing a method of fabricating a core-shell nanowire by chemical vapor deposition (Lincoln J. Lauhon et al., Nature, 2002, 420(6911), pp 57-61). Specifically, when a shell-forming material is repeatedly deposited on a core nanowire fabricated by catalytic decomposition of gold nanoparticles, it is possible to fabricate multiple shells on the nanowire. However, the deposition method requires conditions such as vacuum, high temperature and plasma, and there is a limitation that only materials capable of forming a uniform layer through vapor formation and deposition can be used for coating.

DISCLOSURE

Technical Problem

An object of the present invention is to provide a method of individually fabricating a core-shell nanowire on a tip of an optical fiber, on a substrate, or on a target object located on other materials, the core-shell nanowire having two different characteristics and being size-adjustable.

Technical Solution

The above object is accomplished by a method for fabricating a core-shell structured nanowire including steps of: a) filling a micropipette or nanopipette with a core nanowire material solution; b) bringing the pipette into contact with a desired position on a target object on which a core nanowire is to be formed; c) raising the pipette to evaporate a solvent of the core nanowire material solution, thereby fabricating a core nanowire; d) filling a separate micropipette or nanopipette with a shell nanotube material solution; e) bringing the separate pipette into contact with the tip of the core nanowire; f) lowering the separate pipette along the core nanowire to dip the core nanowire into the solution in the separate pipette; and g) raising the separate pipette to evaporate a solvent of the shell nanotube material solution, thereby fabricating a shell nanotube.

Preferably, the desired position may be an optical fiber tip, any position on a substrate, or any position on any target object.

Preferably, the core nanowire material solution may include: a hydrophilic material selected from the group consisting of poly(acrylic acid), poly(vinyl alcohol), poly (ethylene glycol), alginate, dextran, and polyacrylamide, or a hydrophobic material selected from the group consisting of polystyrene, polycarbonate, polyurethane, and poly(lactic acid); and at least one solvent selected from the group consisting of deionized water, dimethyl sulfoxide, dimethylformamide, toluene, xylene, tetrahydrofuran, ethanol, and chloroform.

Preferably, the shell nanotube material solution may include: a hydrophilic material selected from the group consisting of poly(acrylic acid), poly(vinyl alcohol), poly (ethylene glycol), and polyacrylamide, or a hydrophobic material selected from the group consisting of polystyrene, polycarbonate, polyurethane, and poly(lactic acid); and at least one solvent selected from the group consisting of deionized water, dimethyl sulfoxide, dimethylformamide, toluene, xylene, tetrahydrofuran, ethanol, and chloroform.

Preferably, when the core nanowire material solution includes the hydrophilic material, the shell nanotube material solution may include the hydrophobic material, and when the core nanowire material solution includes the hydrophobic material, the shell nanotube material solution may include the hydrophilic material.

Preferably, the diameters of the core nanowire and the shell nanotube may be adjusted by adjusting the raising speed of the pipette and the separate pipette, respectively.

In addition, the above object is accomplished by a core-shell structured nanowire fabricated by the above method and composed of a core nanowire and a shell nanotube covering the outside of the core nanowire, wherein the diameter of the core nanowire is 100 nm to 10 μm, and the diameter of the shell nanotube is 500 nm to 50 μm.

Preferably, the core-shell structured nanowire may be used for drug delivery, a sensor, or an optical waveguide.

In addition, the above object is accomplished by a core-shell structure nanowire including an optical fiber and composed of the optical fiber, a core nanowire extending from the tip of the optical fiber, and a shell nanotube covering the core nanowire.

Advantageous Effects

The core-shell nanowire fabricated according to the present invention includes a core and shell composed of different materials, and thus may exhibit various and complex properties depending on the materials of the nanowire.

The method for fabricating a core-shell nanowire according to the present invention has significantly improved utility because it is possible to fabricate an individual nanowire at a desired position on a substrate or an optical fiber tip. In addition, the length and diameter of the core-shell nanowire fabricated according to the present invention may be easily adjusted.

MODE FOR INVENTION

Unless otherwise defined, all technical terms used in the present invention have the following definitions and have the same meanings as commonly understood by those skilled in the art to which the present invention pertains. In addition, although a preferred method or sample is described herein, those similar or equivalent thereto are also included in the scope of the present invention.

The present invention is directed to a method for fabricating a core-shell structured nanowire including steps of:

a) filling a micropipette or nanopipette with a core nanowire material solution; b) bringing the pipette into contact with a desired position; c) raising the pipette to evaporate a solvent of the core nanowire material solution, thereby fabricating a core nanowire; d) filling a separate micropipette or nanopipette with a shell nanotube material solution; e) bringing the separate pipette into contact with the tip of the core nanowire; f) lowering the separate pipette along the core nanowire to dip the core nanowire into the solution in the separate pipette; and g) raising the separate pipette to evaporate a solvent of the shell nanotube material solution, thereby fabricating a shell nanotube.

Hereinafter, each step will be described in detail.

First, a micropipette or nanopipette is filled with a core nanowire material solution (step a). The solute contained in the core nanowire material solution includes any material, and preferably includes a hydrophilic material or a hydrophobic material. Specifically, as the hydrophilic material, a material such as poly(acrylic acid), poly(vinyl alcohol), poly(ethylene glycol), alginate, dextran, or polyacrylamide may be used. In addition, a mixture of the hydrophilic materials or a gel obtained by crosslinking the hydrophilic material may also be used. As the hydrophobic material, a material such as polystyrene, polycarbonate, polyurethane, poly(lactic acid), or poly(methyl methacrylate) may be used. In addition, a mixture of the hydrophobic materials or a gel obtained by crosslinking the hydrophobic material may also be used. As a solvent of the nanowire material solution, a material capable of dissolving the solute and evaporating easily may be used. For example, the solvent may be at least one selected from the group consisting of DI water, dimethyl sulfoxide (DMSO), dimethylformamide (DMF), toluene, xylene, tetrahydrofuran (THF), ethanol (EtOH), and chloroform.

Next, the pipette is brought into contact with a desired position on a target object on which the nanowire is to be formed (step b).

Figure 1:
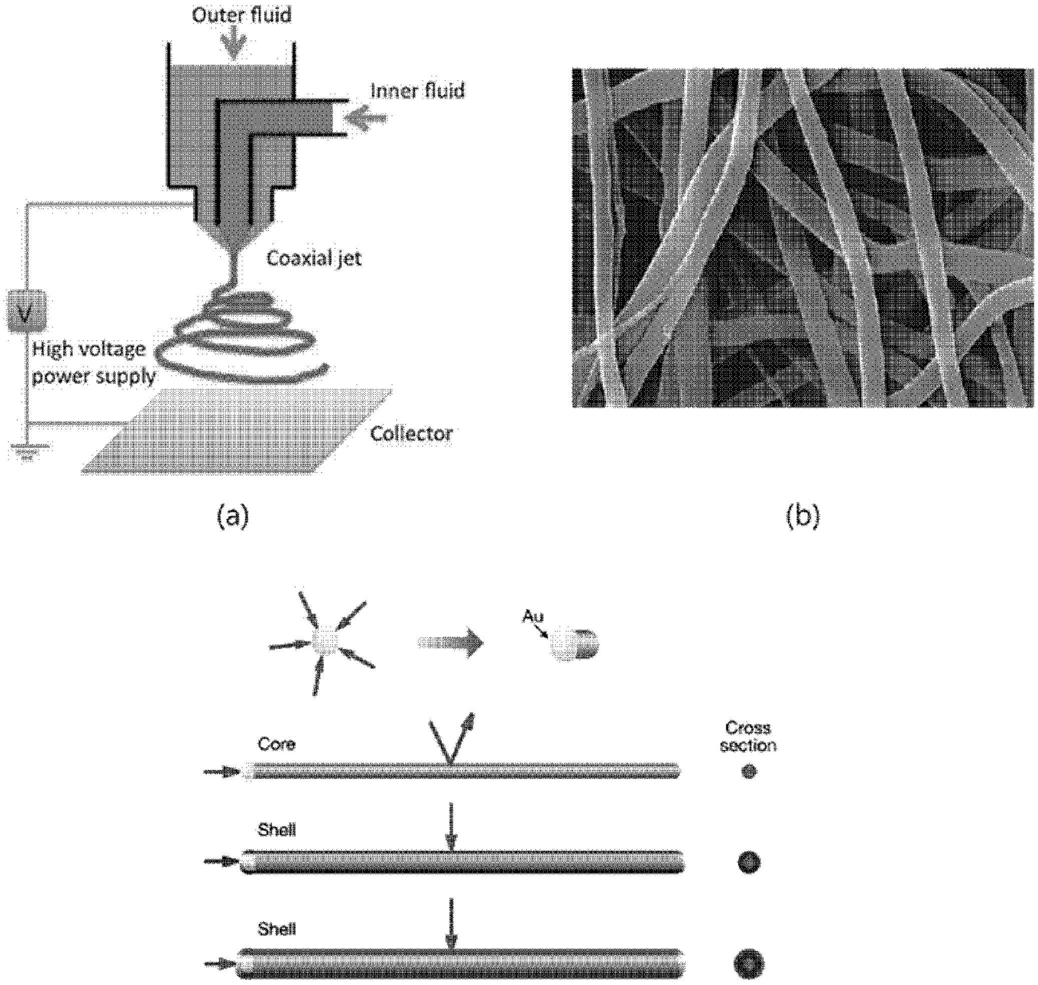
FIG. 1 Prior Art
FIG. 1 shows conventional methods for fabricating a core-shell nanowire. (a) shows a method of fabricating a core-shell nanowire through coaxial electrospinning, (b) is an image of nanowires fabricated on a substrate by coaxial electrospinning, and (c) shows a method of fabricating a core-shell nanowire by deposition.
Figure 2:
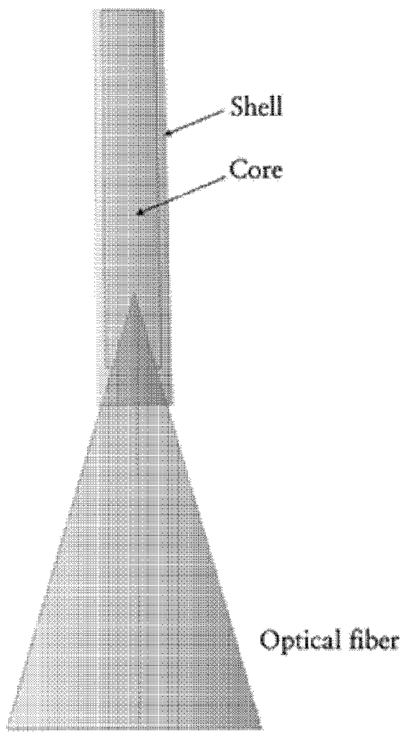
FIG. 2 shows the structure of a core-shell nanowire. Here, the core-shell nanowire is composed of: a core nanowire grown on an object such as an optical fiber; and a shell nanotube covering the core nanowire.
Figure 3:
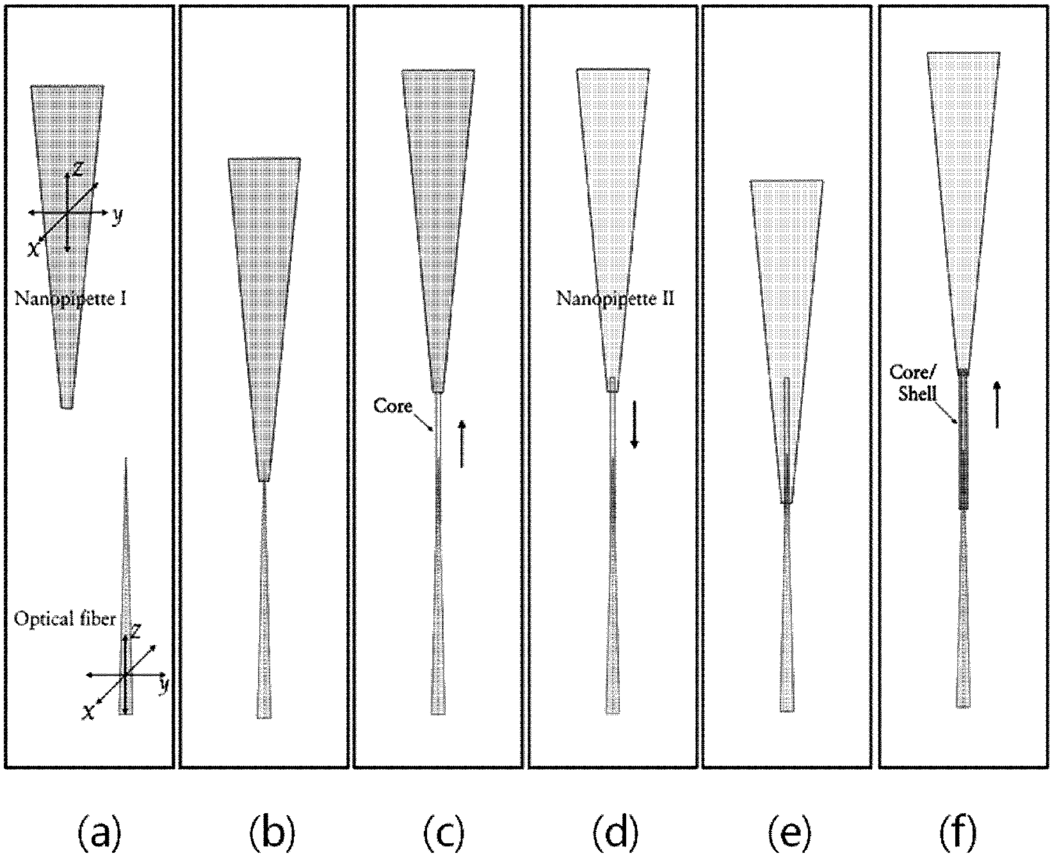
FIG. 3 shows a process for fabricating a core-shell nanowire.

FIGS. 3(*a*) and 3(*b*) show that the tip of the pipette is brought into contact with the tip of an optical fiber. To bring the tapered optical fiber tip into contact with the tip of the pipette, it is preferable to move the optical fiber to the foci of two optical lenses (which are aligned to the x-axis and y-axis, respectively, such that the foci are at the same point) by moving the optical fiber along the x-, y- and z-axes (FIG. 3(*a*)). Next, it is preferable to move the pipette to the tip of the optical fiber by moving the pipette along the x-, y-, and z-axis (FIG. 3(*b*)). Here, it is preferable that the tip of the optical fiber is slightly inserted into the inside of the tip of the pipette.

Next, a core nanowire is fabricated by raising the pipette, simultaneously allowing to evaporate the solvent of the core nanowire material solution (step c). FIG. 3(*c*) shows fabricating the core nanowire by raising the pipette. Specifically, when the pipette is raised, the inner liquid is rapidly evaporated and the dissolved material is solidified to form a columnar shape. The pipette is preferably raised in the z-axis direction.

Next, a step of filling a separate micropipette or nanopipette with a shell nanotube material solution (step d) is performed.

The solute contained in the cell nanotube material solution includes any material, and preferably includes a hydrophobic material or a hydrophilic material. As the hydrophobic material, a material such as polystyrene, polycarbonate, polyurethane, poly(lactic acid), or poly(methyl methacrylate) may be used. In addition, a mixture of the hydrophobic materials or a gel obtained by crosslinking the hydrophobic material may also be used. Specifically, as the hydrophilic material, a material such as poly(acrylic acid), poly(vinyl alcohol), poly(ethylene glycol), alginate, dextran or polyacrylamide may be used. In addition, a mixture of the hydrophobic materials or a gel obtained by crosslinking the hydrophobic material may also be used. As a solvent of the nanowire material solution, a material capable of dissolving the solute and evaporating easily may be used. For example, the solvent may be at least one selected from the group consisting of DI water, dimethyl sulfoxide (DMSO), dimethylformamide (DMF), toluene, xylene, tetrahydrofuran (THF), ethanol (EtOH), and chloroform.

The nanowire has a uniform and stable structure by van der Waals bonds acting between polymers constituting the nanowire. Here, as the strength of the van der Waals bond increases with the increase in the molecular weight, it is preferable to use a polymer having a molecular weight of 5,000 to 200,000 as the hydrophilic or hydrophobic material. The van der Waals force depends on the molecular weight and the presence or absence of polarity in the molecule, and is used as a factor determining the solubility of the compound. A hydrophilic polymer is readily soluble in a polar solvent, but is insoluble in a non-polar solvent. On the other hand, a hydrophobic polymer is readily soluble in a non-polar solvent, but is insoluble in a polar solvent.

Thus, when a hydrophilic material is used in the core nanowire material solution, the shell nanotube material solution preferably includes a hydrophobic material. Conversely, when a hydrophobic material is used for the core nanowire material solution, the shell nanotube material solution preferably includes a hydrophilic material.

Next, as shown in FIG. 3(*d*), the separate pipette is brought into contact with the tip of the core nanowire (step e).

Next, as indicated by the arrow in FIG. 3(*d*), the pipette is lowered along the core nanowire to dip the core nanowire into the shell nanotube material solution (step f). FIG. 3(*e*) shows that the core nanowire is dipped into the shell nanotube material solution in the separate pipette.

Next, a shell nanotube is fabricated by raising the separate pipette to evaporate the solvent of the shell nanotube material solution (step g). FIG. 3(*f*) shows fabricating the shell nanotube by raising the separate pipette. Specifically, when the separate pipette is raised, the inner liquid is rapidly evaporated and the dissolved material is solidified to form a tube shape. The separate pipette is preferably raised in the z-axis direction.

Next, the diameters of each of the core nanowire and the shell nanotube fabricated by the method shown in FIG. 3 is determined by the inner diameter of the tip of the pipette and the rising speed of the pipette.

Preferably, in the nanowire of the core-shell structured nanowire fabricated according to the present invention, the diameter of the core may be 100 nm to 10 μm, and the diameter of the shell may be 500 nm to 50 μm. More preferably, the diameter of the core may be 200 nm to 500 nm, and the diameter of the shell may be 600 nm to 1 μm.

Figure 4:
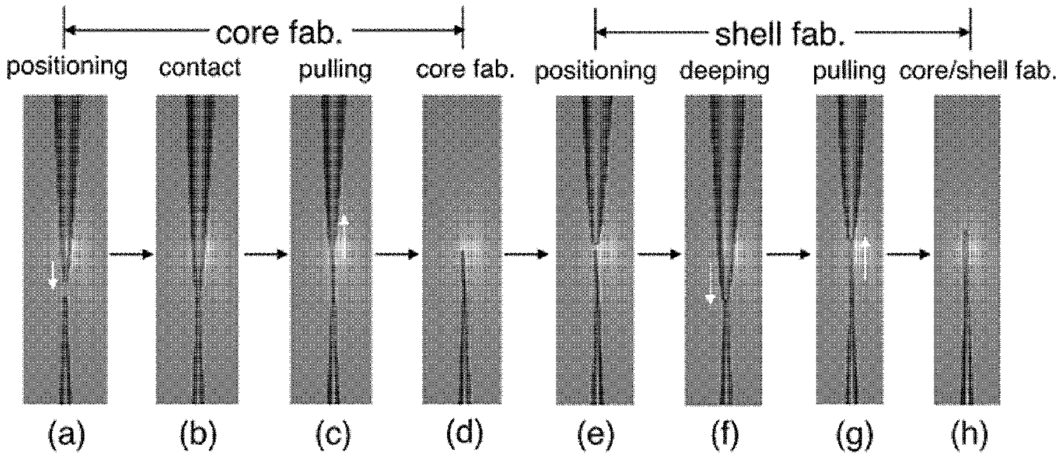
FIG. 4 shows a process of fabricating a core-shell nanowire on an optical fiber.

FIG. 4 shows the overall process of fabricating a core-shell nanowire at the tip of a tapered optical fiber by the above-described method. According to the process shown in FIG. 4, it is possible to obtain a core-shell structured nanowire including an optical fiber and composed of the optical fiber, a core nanowire extending from the tip of the optical fiber, and a shell nanotube covering the core nanowire.

Figure 5:
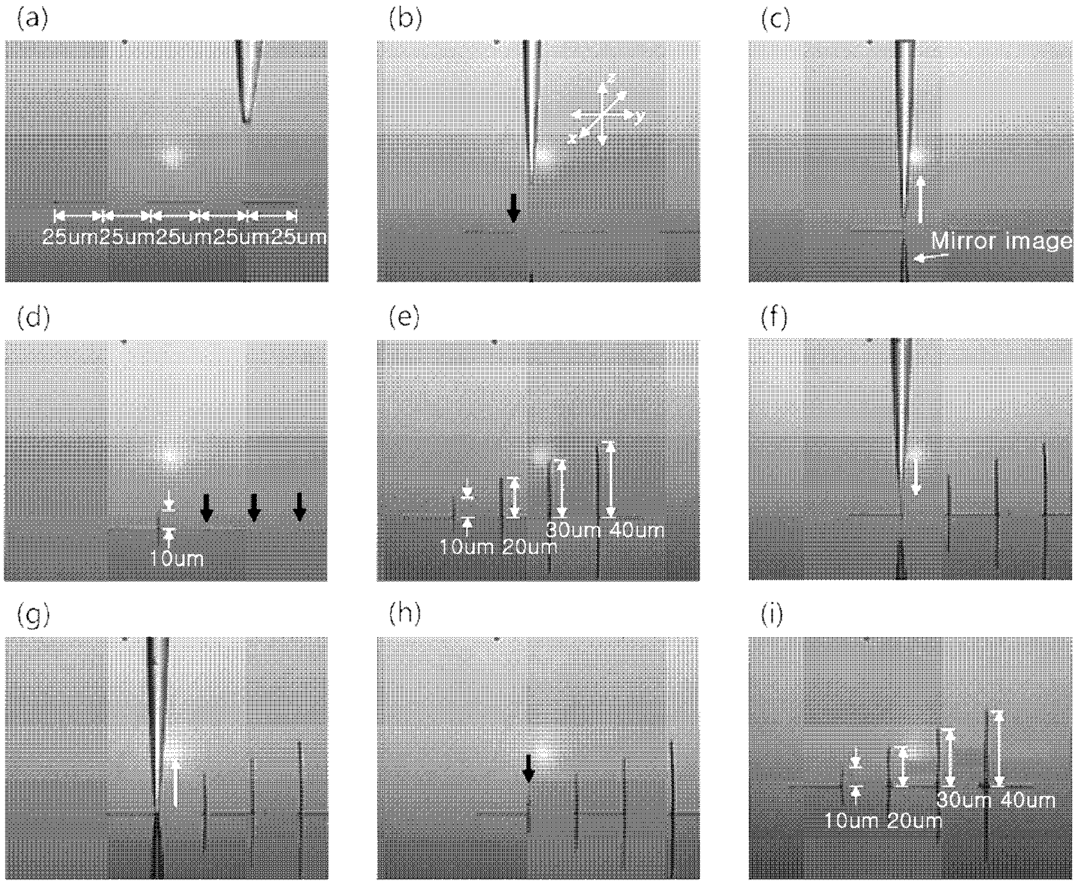
FIG. 5 shows a process of fabricating a core-shell nanowire on a substrate.

FIG. 5 shows the overall process of fabricating a core-shell nanowire having a desired length at a specific position on a substrate. FIG. 5(*a*) shows a silicon substrate on which linear patterns having a length of 25 μm and a spacing of 25 μm are printed. In order to fabricate a core-shell nanowire at a specific position on the substrate, it is preferable to move the pipette filled with the nanowire material solution and the substrate along the x-, y- and z-axis, such that the tip of the pipette reaches a specific position on the substrate. For example, in order to fabricate a nanowire at the point indicated by the red arrow in FIG. 5(*b*), it is preferable to move the pipette filled with the core nanowire material solution, thereby bringing the tip of the pipette into contact with the point. In case that light is easily reflected from the surface of the substrate, whether the pipette is in contact with the substrate or not can be more easily confirmed by observing the tip of the pipette and the tip of the pipette reflected on the substrate as shown in FIG. 5(*c*).

Next, FIG. 5(*c*) shows a step of fabricating a core nanowire having a specific length by raising the pipette to a specific height. FIG. 5(*d*) shows a core nanowire having a length of 10 μm, fabricated on the substrate. FIG. 5(*e*) shows core nanowires having lengths of 20, 30, and 40 μm, respectively, in orderfrom the left, and a diameter of 500 nm or less, fabricated at the points indicated by the red arrows in FIG. 5(*d*).

Next, as indicated by the arrow in FIG. 5(*f*), the pipette filled with the shell nanotube material solution is coaxially aligned with the core nanowire, and then is lowered along the core nanowire to dip the nanowire into the solution in the pipette. FIG. 5(*g*) shows the core nanowire dipped into the solution in the pipette.

Next, the pipette is raised to a desired height, thereby fabricating a shell nanotube. The nanowire indicated by the red arrow in FIG. 5(*h*) is a core-shell nanowire fabricated by covering the core nanowire with the shell nanotube.

FIG. 5(*i*) shows core-shell nanowires fabricated by the above-described method. The lengths of the nanowires on the substrate are 10, 20, 30, and 40 μm in order from the left, the diameter thereof is 1 μm or less, and the spacing between the nanowires is 25 μm.

Figure 6:
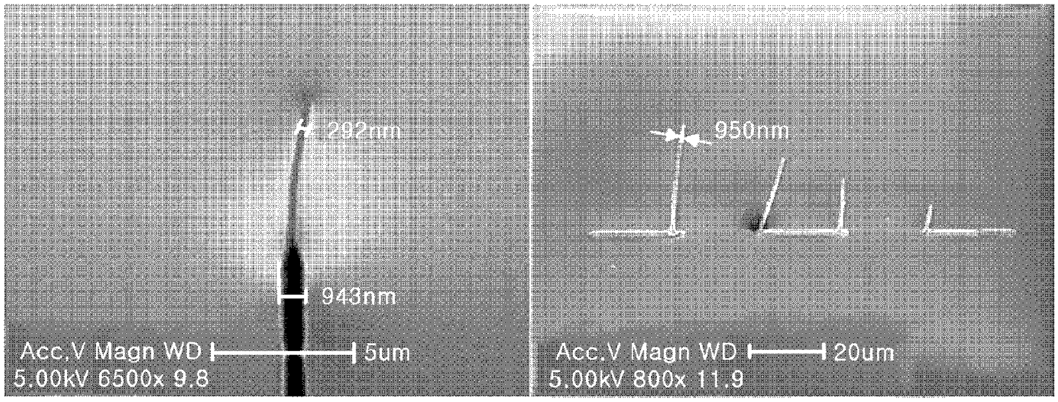
FIG. 6 is (a) an FE-SEM photograph of a core-shell nanowire fabricated on an optical fiber, and (b) an FE-SEM photograph of a core-shell nanowire fabricated on a substrate.

FIG. 6(*a*) shows an SEM image taken after fabricating a core-shell nanowire on an optical fiber so that the axes of the core nanowire and the shell nanotube coincide with each other, and by removing a top portion of the shell nanotube a top portion of the core nanowire is exposed. It can be seen that the diameter of the core nanowire is as small as 292 nm, and the diameter of the shell nanotube covering the core nanowire is 943 nm, which is larger than that of the core nanowire.

FIG. 6(*b*) shows an SEM photograph of core-shell nanowires fabricated on a substrate on which patternsare printed. The diameter of the core-shell nanowires on the substrate is 950 nm, the lengthsthereof are 40, 30, 20 and 10 μm in order from the left, and the spacing between the nanowires is 25 μm.

Figure 7:
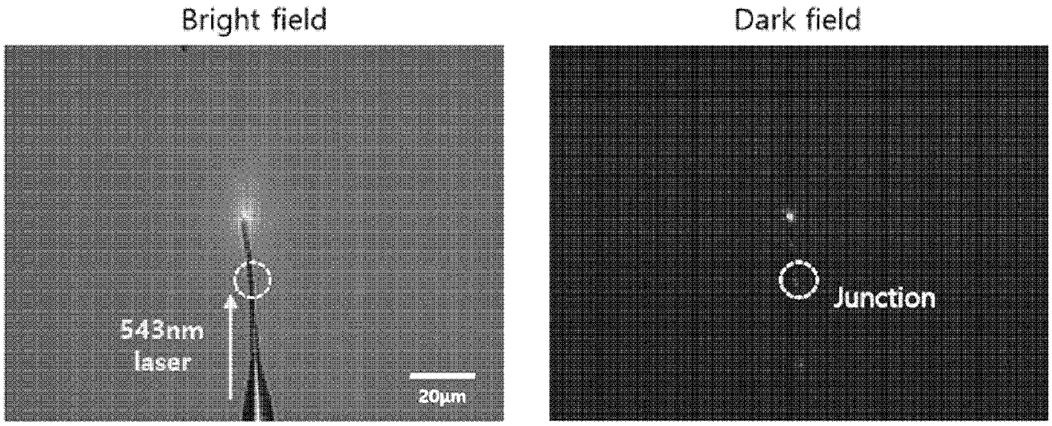
FIG. 7 shows a microscope image obtained when light having a wavelength of 543 nm was injected through an optical fiber into a core-shell nanowire fabricated on the optical fiber.

FIG. 7 shows a microscope image obtained when light having a wavelength of 543 nm was injected through the optical fiber on one tip of which a core-shell nanowire has been fabricated. It can be seen that light scattering did not occur at the junction between the nanowire and the optical fiber, suggesting that the junction is optically coupled very well. In addition, it can be confirmed that light was transmitted well to the tip of the core-shell nanowire. Therefore, when a photoreactive polymer or a fluorescent dye is used as a material constituting the core-shell nanowire, the core-shell nanowire may be applied to drug delivery, sensors, optical waveguides, and the like.

Hereinafter, the present invention will be described in detail with reference to examples, but the scope of the present invention is not limited by these examples.

EXAMPLE 1

Among materials to be used in the experiment, poly (acrylic acid) (average molecular weight (Mw): 100,000), polystyrene (average molecular weight (Mw): 90,000), and toluene were purchased from Sigma-Aldrich (USA) and used without further purification. First, a core nanowire material solution was prepared by dissolving poly(acrylic acid) in distilled water at a concentration of 1 wt %. Next, a shell nanotube material solution was prepared by dissolving polystyrene in toluene at a concentration of 1 wt %.

Next, a nanopipette was fabricated using a pipette puller (P-97, Sutter Instrument). Then, a tapered optical fiber was fabricated using a laser-based puller (P-2000, Sutter Instrument). An x-y-z stepping motor (KOHZU Precision) with a spatial resolution of 250 nm was used to control positions of the nanopipette and the optical fiber.

First, a nanopipette filled with the core nanowire-forming material and the optical fiber were aligned with each other (FIG. 4(*a*)). Then, the nanopipette and the tip of the optical fiber were brought into contact with each other (FIG. 4(*b*)), and the nanopipette was raised by 20 μm in the z-axis direction at a speed of 25 μm/s to evaporate the solvent of the core nanowire-forming material solution, thereby fabricating a core nanowire (FIGS. 4(*c*) and 4(*d*)). Then, a nanopipette filled with the shell nanotube material solution and the core nanowire were aligned with each other (FIG. 4(*e*)), and the core nanowire was put into the inside of the nanopipette and thereby overlapped therewith (FIG. 4(*f*)). The nanopipette was raised by 20 μm in the z-axis direction at a speed of 10 μm/s to evaporate the solvent of the shell nanotube material solution, thereby fabricating a shell nanotube (FIGS. 4(*g*) and 4(*h*)).

EXAMPLE 2

Materials and nanopipettes to be used in the experiment were prepared in the same manner as in Example 1.

Linear patterns with a length of 25 μm and a spacing of 25 μm were printed on a silicon substrate using a nanopipette filled with a shell nanotube material solution (FIG. 5*a*). A nanopipette filled with a core nanowire-forming material solution was brought into contact with the substrate at desired positions, and then raised by 10 μm, 20 μm, 30 μm and 40 μm, respectively, at a speed of 25 μm/s, thereby fabricating core nanowires (FIGS. 5(*b*), 5(*c*), 5(*d*) and 5(*e*)). The pipette filled with the shell nanotube material solution was aligned with the core nanowires on the substrate so that the core nanowires on the substrate entered the inside of the pipette, and then raised by 10, 20, 30 and 40 μm, respectively, at a speed of 25 μm/s, thereby fabricating shell nanotubes and finally fabricating core-shell nanowires (FIGS. 5(*b*), 5(*c*), 5(*d*) and 5(*e*)). and when the core nanowire comprises a hydrophobic material, the shell nanotube comprises a hydrophilic material.

11. The core-shell structured nanowire of claim 8, wherein the hydrophilic material is selected from the group consisting of poly(acrylic acid), poly(vinyl alcohol), poly (ethylene glycol), alginate, dextran, and polyacrylamide, and the hydrophobic material is selected from the group consisting of polystyrene, polycarbonate, polyurethane, poly (lactic acid), and poly(methyl methacrylate).

12. A core-shell structured nanowire comprising an optical fiber and composed of the optical fiber, a core nanowire extending from a tip of the optical fiber, and a shell nanotube covering the core nanowire.

The invention claimed is:

1. A method for fabricating a core-shell structured nanowire comprising steps of:

a) filling a first micropipette or a first nanopipette with a core nanowire material solution;

b) bringing the first micropipette or the first nanopipette into contact with a desired position on a target object on which a core nanowire is to be formed;

c) raising the first micropipette or the first nanopipette to evaporate a solvent of the core nanowire material solution, thereby fabricating the core nanowire;

d) filling a second micropipette or a second nanopipette with a shell nanotube material solution;

e) bringing the second micropipette or the second nanopipette into contact with a tip of the core nanowire;

f) lowering the second micropipette or the second nanopipette along the core nanowire to dip the core nanowire into the shell nanotube material solution in the second micropipette or the second nanopipette; and g) raising the second micropipette or the second nanopipette to evaporate a solvent of the shell nanotube material solution, thereby fabricating a shell nanotube.

2. The method of claim 1, wherein the desired position is an optical fiber tip, any position on a substrate, or any position on any target object.

3. The method of claim 1, wherein the core nanowire material solution comprises: a hydrophilic material selected from the group consisting of poly(acrylic acid), poly(vinyl alcohol), poly(ethylene glycol), alginate, dextran, and polyacrylamide, or a hydrophobic material selected from the group consisting of polystyrene, polycarbonate, polyurethane, poly(lactic acid), and poly(methyl methacrylate); and at least one solvent selected from the group consisting of deionized water, dimethyl sulfoxide, dimethylformamide, toluene, xylene, tetrahydrofuran, ethanol, and chloroform.

4. The method of claim 1, wherein the shell nanotube material solution comprises: a hydrophilic material selected from the group consisting of poly(acrylic acid), poly(vinyl alcohol), poly(ethylene glycol), alginate, dextran, and polyacrylamide, or a hydrophobic material selected from the group consisting of polystyrene, polycarbonate, polyurethane, poly(lactic acid), and poly(methyl methacrylate); and at least one solvent selected from the group consisting of deionized water, dimethyl sulfoxide, dimethylformamide, toluene, xylene, tetrahydrofuran, ethanol, and chloroform.

5. The method of claim 3, wherein, when the core nanowire material solution comprises the hydrophilic material, the shell nanotube material solution comprises the hydrophobic material.

6. The method of claim 3, wherein, when the core nanowire material solution comprises the hydrophobic material, the shell nanotube material solution comprises the hydrophilic material.

7. The method of claim 1, wherein a diameter of each of the core nanowire and the shell nanotube is adjusted by adjusting a raising speed of the first micropipette or the first nanopipette, and a raising speed of the second micropipette or the second nanopipette, respectively.

8. A core-shell structured nanowire fabricated by the method of claim 1 and composed of a core nanowire and a shell nanotube covering an outside of the core nanowire, wherein the core nanowire has a diameter of 100 nm to 10 μm, and the shell nanotube has a diameter of 500 nm to 50 μm.

9. The core-shell structured nanowire of claim 8, which is used for drug delivery, a sensor, or an optical waveguide.

10. The core-shell structured nanowire of claim 8, wherein, when the core nanowire comprises a hydrophilic material, the shell nanotube comprises a hydrophobic material, and when the core nanowire comprises a hydrophobic material, the shell nanotube comprises a hydrophilic material.

11. The core-shell structured nanowire of claim 10, wherein the hydrophilic material is selected from the group consisting of poly(acrylic acid), poly(vinyl alcohol), poly (ethylene glycol), alginate, dextran, and polyacrylamide, and the hydrophobic material is selected from the group consisting of polystyrene, polycarbonate, polyurethane, poly (lactic acid), and poly(methyl methacrylate).

12. A core-shell structured nanowire fabricated according to the method of claim 1 comprising an optical fiber and composed of the optical fiber, a core nanowire extending from a tip of the optical fiber, and a shell nanotube covering the core nanowire.

13. The method of claim 3, wherein, when the core nanowire material solution comprises the hydrophilic material, the shell nanotube material solution comprises the hydrophobic material.

* * * * *